United States Patent [19]
Schmidt

[11] Patent Number: 5,116,326
[45] Date of Patent: May 26, 1992

[54] HYPODERMIC NEEDLE SHEATH

[75] Inventor: David A. Schmidt, Bay City, Mich.

[73] Assignee: Schmidt Industries, Inc., Bay City, Mich.

[21] Appl. No.: 691,085

[22] Filed: Apr. 25, 1991

[51] Int. Cl.⁵ .............................................. A61M 5/32
[52] U.S. Cl. ..................................... 604/198; 604/263
[58] Field of Search ............... 604/198, 263, 187, 192, 604/207, 208, 220

[56] References Cited
U.S. PATENT DOCUMENTS

| | | | |
|---|---|---|---|
| 4,915,696 | 4/1990 | Feimer | 604/192 |
| 4,927,416 | 5/1990 | Tomkiel | 604/263 X |
| 4,932,947 | 6/1990 | Cardwell | 604/198 |
| 4,946,447 | 8/1990 | Hardcastle et al. | 604/263 X |
| 5,013,302 | 5/1991 | Schmidt | 604/198 |

Primary Examiner—John D. Yasko
Attorney, Agent, or Firm—Learman & McCulloch

[57] ABSTRACT

A protective sheath for use with a hypodermic needle comprises a tubular body for accommodating the needle and at least a portion of the syringe barrel adjacent the needle. The sheath is latched in protective relation on the syringe, but may be released by rotation relative to the syringe or by deflection of part of the latch.

18 Claims, 2 Drawing Sheets

HYPODERMIC NEEDLE SHEATH

This invention relates to a protective sheath for a hypodermic needle which is movable from a latched, safety position in which the needle is fully encased within the sheath to a second latched position in which the needle is exposed for use.

BACKGROUND OF THE INVENTION

The use of hypodermic needles subjects the user to considerable risk of contracting a disease or disorder in the event the user pricks his or her finger following use of the hypodermic needle on such other person. In like manner, the person upon whom the hypodermic needle is used by another person is subjected to the same risk if the user has a communicable disease and pricks his or her finger prior to use of the needle.

The prior art contains many proposals for protecting the users of hypodermic needles against inadvertent pricking by the needle. Some of the proposals have included flexible or collapsible covers which overlie the needle, others have included shields or guards which encircle the needle, and still others comprise pads in which the top of the needle may be embedded. Most, if not all, of the known protective devices require manipulation of the shield or guard by the hands of the user and in such manner that the user's fingers must pass very close to the needle tip, thereby exposing the user to the risk of being pricked by the needle. The exposure to risk is increased in those instances in which the shield is flexible, or collapsible, or consists simply of a pad of spongy material.

Protective devices constructed in accordance with the invention overcome the disadvantages referred to above by utilizing relatively rigid shields of such size as to accommodate not only the entire needle, but also a substantial portion of the syringe from which the needle projects. The length of the shield and its rigidity make possible placement of the user's fingers on the shield in an area remote from the tip of the needle. The rigidity of the shield minimizes greatly the risk that the needle will penetrate the shield as the latter is applied to or removed from the syringe. Finally, the shield is latched in its protective position, thereby minimizing the possibility of inadvertent exposure of the needle. The shield may be released from its latched, protective condition either by relative rotation of the shield and the syringe or by deflection of the latching part of the shield.

SUMMARY OF THE INVENTION

A protective sheath for use in conjunction with a hypodermic needle comprises an elongate, tubular body formed of resilient material such as polyethylene, polypropylene, or other suitable plastic, and is of such diameter as slideably to accommodate the syringe of a hypodermic needle with the needle wholly contained within the sheath.

The sheath is releasably latched in its safety position from which the sheath is movable to a position in which the needle is exposed for use. The latch comprises an extension on the shield which is cooperable with a flange on the syringe to maintain the sheath in either of the safety or exposed positions. Preferably, the sheath remains in latched assembly with the syringe regardless of whether the needle is exposed or confined within the sheath.

The sheath is of sufficient rigidity to resist penetration by the needle and, correspondingly, to prevent deflection of the sheath to such an extent as to bend or otherwise damage the needle.

The free end of the needle is protected by a membrane which the needle may pierce when the syringe is prepared for use.

THE DRAWINGS

A preferred embodiment of the invention is disclosed in the accompanying drawings wherein.

THE DISCLOSED EMBODIMENTS

Figure 2:
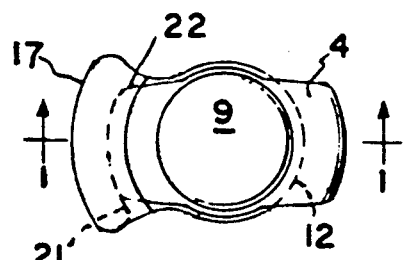
FIG. 2 is a top plan view of the embodiment shown in FIG. 1.
Figure 4:
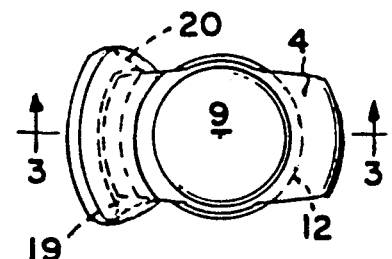
FIG. 4 is a top plan view of the construction shown in FIG. 3.

Apparatus constructed in accordance with the embodiment of the invention shown in FIGS. 1-8 is adapted for use in conjunction with a conventional hypodermic needle 1 comprising a syringe 2 composed of a tubular barrel 3 having a discontinuous, peripheral, generally rectangular flange 4 at one end and terminating at its other end in a fitting 5 in which is secured one end of a hollow needle 6 that extends in prolongation of the syringe barrel. The needle 6 has a free distal end 7 as is conventional. Slideably accommodated in the barrel is a reciprocable piston 8 terminating at its outer end in a thumb seat 9. The piston 8 may or may not be rotatable within the barrel 3, as desired, and is of such diameter that movement of the piston in one direction enables the contents of the barrel to be discharged through the needle 6, whereas movement of the piston in the opposite direction enables fluid to be introduced to the barrel via the needle. As thus far described, the syringe 2, the fitting 5, and the needle 6 are conventional.

The embodiment of the invention shown in FIGS. 1-4 includes a protective, annular sheath 10 having an elongate, tubular body 11 formed of a rigid, resilient plastic material and having an annular side wall 12 terminating at one end in a frustoconical section 13 joined to an annular tip 14 having a passage 15 therethrough of such cross sectional area as freely to accommodate the needle 6. At its opposite end the body 11 is open. The inside diameter of the body wall 12 is of such cross sectional area as freely to accommodate the barrel 3 of the syringe 2 and the length of the body 11 is sufficient to enable the needle 6, the fitting 5, and a substantial portion of the barrel 3 to be accommodated wholly within the confines of the body 11.

The body 12 of the protective sheath 10 terminates at that end opposite the tip 14 in a flexible hinge 16a. Coupled to the hinge is an arcuate extension 16 which subtends an angle of about 80° and having an outward convex surface 17 and an inner concave surface 18. Adjacent the juncture of the extension 16 with the body side wall 12 the extension has a discontinuous, circumferential groove 19 in its inner surface 18. The groove 19 has an abutment or shoulder 20 adjacent one end, but is open at its other end. Adjacent its outer or free end the inner surface 18 of the extension 16 has therein a discontinuous groove 21 open at one end and closed at its other end by an abutment 22. The width or height of each groove 19 and 21 is sufficient to accommodate freely the flange 4 of the barrel 3. The spacing between the grooves 19 and 21 corresponds to a substantial portion of the length of the needle 6.

Figure 1:
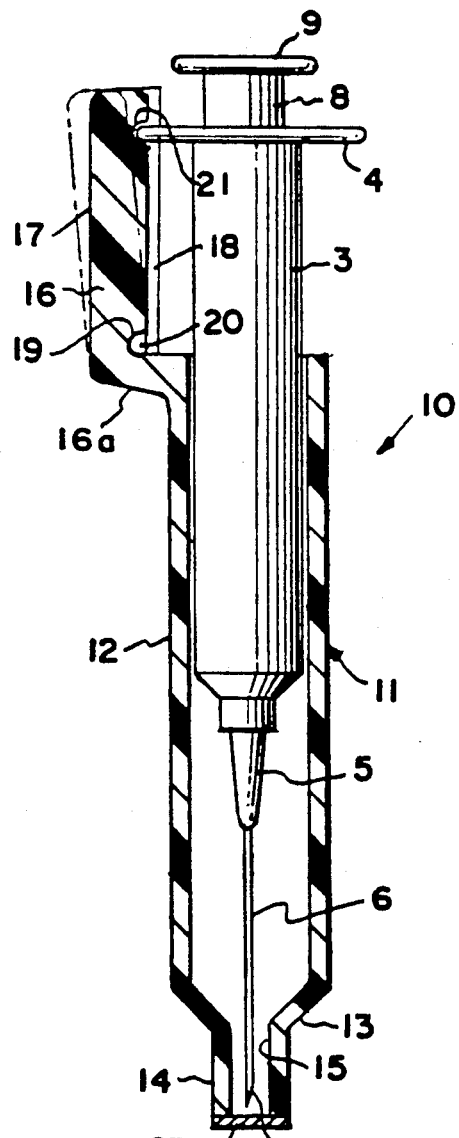
FIG. 1 is a vertical sectional view taken on the line 1—1 of FIG. 2 of a hypodermic needle and protective sheath and illustrating the needle in a retracted, safety position.

The bore of the sheath 11 is of such size as freely to accommodate the syringe 2 of the hypodermic needle 1 and is of such length as wholly to accommodate the needle 6 and a substantial portion of the syringe barrel 3, as is shown in FIG. 1.

Preferably, a membrane 23 overlies and seals the passage 15 until the syringe is ready for use so as to protect the free end 7 of the needle 6.

To assemble the hypodermic needle 1 and the sheath 11, the needle 6 and the syringe barrel 3 are introduced to the sheath from the open end thereof. During assembly the flange 4 is 90° spaced from the position shown in FIG. 1 to enable the syringe to be moved into the sheath 11 a distance such that the flange 4 is at the level of the groove 21, whereupon the syringe may be rotated to the position shown in FIG. 1 in which the flange 4 is accommodated in the groove 19 and abuts the abutment 22. In these positions of the parts the syringe barrel and the needle 6 will be latched against axial movement in either direction relative to the sheath 11. The flange 4 thus constitutes one part of a latching means and the groove 21 constitutes a second part of such latching means.

Figure 3:
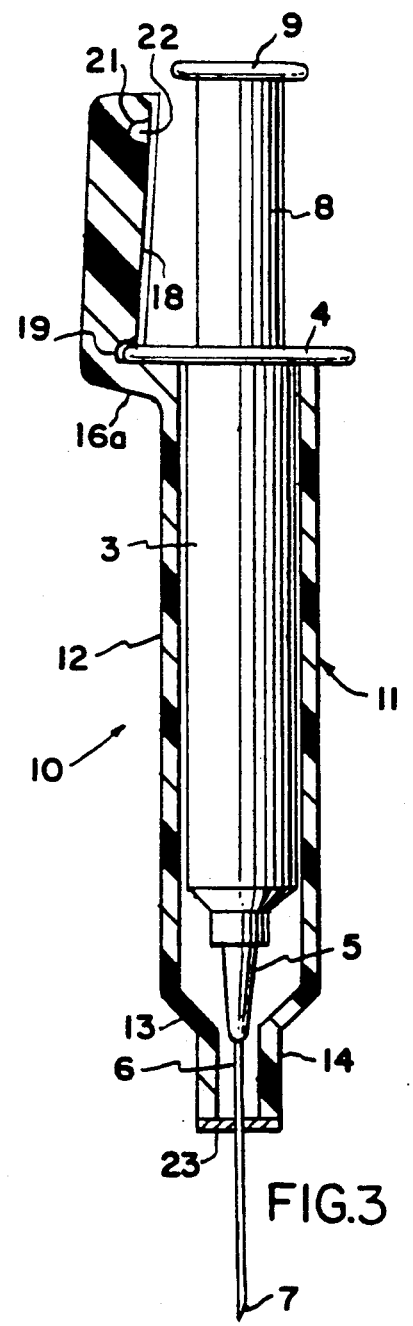
FIG. 3 is a view similar to FIG. 1 taken on the line 3—3 of FIG. 4, but illustrating the hypodermic needle adjusted relative to the sheath so as to enable the needle to be projected therefrom.

When it is desired to make use of the hypodermic needle, the syringe may be rotated counterclockwise from the position shown in FIG. 1 to remove the flange wholly from the slot 19, following which the hypodermic needle may be moved downwardly relative to the sheath 11 from the position shown in FIG. 1 to the position shown in FIG. 3, whereupon a substantial portion of the needle 6 is projected beyond the sheath. The needle 6 pierces the membrane 23. The syringe then may be rotated clockwise to the position shown in FIG. 4 whereupon the flange 4 will enter the slot 19 and move therein until it engages the abutment 20. The hypodermic needle thus will be latched in place in a position in which the needle is exposed for use. After use, the hypodermic needle may be returned to the position shown in FIG. 1.

If desired, of course, the hypodermic needle 1 may be removed completely from the sheath following disengagement of the flange 4 from the groove 21.

In the preferred embodiment of the invention the material from which the sheath 11 is formed is of such resilience as to enable the hinge 16a to flex and deflect the extension 16 outwardly from the position shown in full lines in FIG. 1 to the position shown in dotted lines. The extent of the deflection should be such as to remove the flange 4 from the groove 21, thereby releasing the syringe for axial movement wholly out of the sheath or to the position shown in FIG. 3 without necessitating rotation of the sheath or the hypodermic needle. As the barrel 3 moves to the position shown in FIG. 3, the flange will cam the extension outwardly until the flange registers with the groove 19 whereupon the resilience of the hinge will cause the extension to move inwardly and seat the flange 4 in the groove 19.

As clearly is shown in FIG. 3 the hinge 16a has an unstressed position in which it biases the extension 16 toward the syringe. The flange 4 thus may be yieldably seated in each of the respective grooves in either position of the syringe. Since the wall of the extension 16 is arcuate and convex outwardly, such wall will resist outward or unlatching deflection of the extension.

In the embodiment shown in FIGS. 5-8 the hypodermic needle 1 is the same as that described earlier, so corresponding reference characters are used to identify corresponding parts.

The hypodermic needle is adapted for use with a sheath 25 which is similar to the sheath 10 and has a body 26 open at one end and terminating at its opposite end in a reduced diameter, annular tip 27 through which the needle 6 may pass. The body includes at its open end an extension 28 joined to the body 26 by a laterally extending hinge or web 29. The extension has a groove 30 at its juncture with the web 29 and thickens toward its free end 31.

Figure 6:
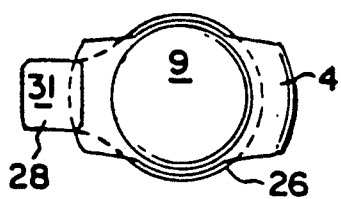
FIG. 6 is a top plan view of the apparatus shown in FIG. 5.
Figure 8:
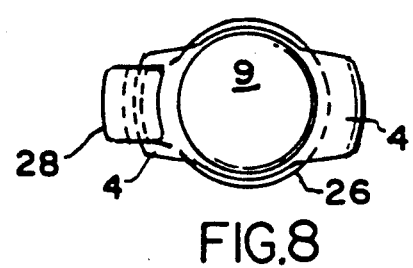
FIG. 8 is a top plan view of the apparatus of FIG. 7.

Adjacent the free end 31 that surface 32 of the extension which confronts the hypodermic needle has a latching groove 33 of such width as freely to accommodate the flange 4. The groove is open at both of its ends; i.e., it has no abutments. As clearly is shown in FIGS. 6 and 8, the peripheral length of the extension 28 is less than that of the flange 4 of the barrel 3.

Figure 5:
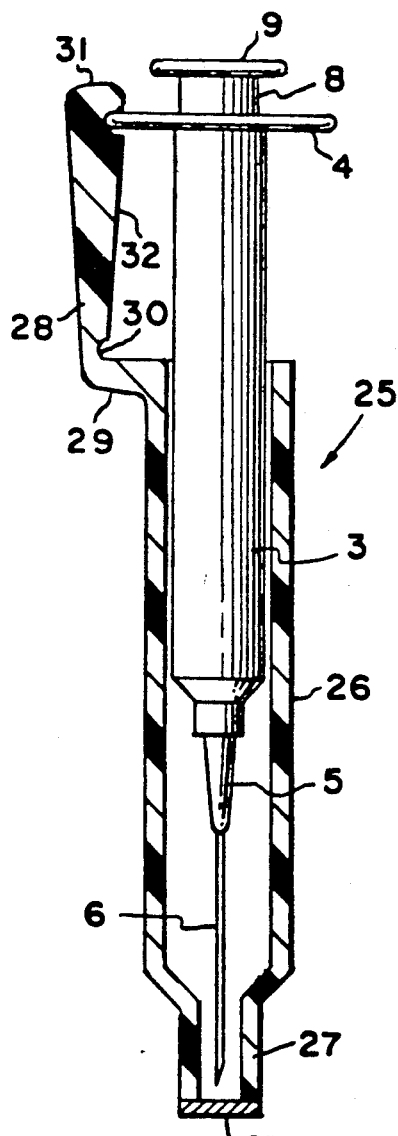
FIG. 5 is a view similar to FIG. 2, but illustrating a further embodiment.

The hypodermic needle 1 may be secured in the safety position shown in FIG. 5 by fitting the flange 4 of the syringe barrel in the groove 33. The extension has a normal, unstressed position in which its free end 31 is inclined toward the syringe, as is shown in full lines in FIG. 7. When the flange 4 is seated in the groove 33, however, the extension is displaced outwardly as is permitted by the flexibility of the hinge formed by the juncture of the extension 28 and the web 29. This position of the extension is shown in FIG. 5. The resilience of the material from which the sheath is formed constantly urges the extension toward the syringe so as yieldably to maintain the flange 4 seated in the groove 33.

Figure 7:
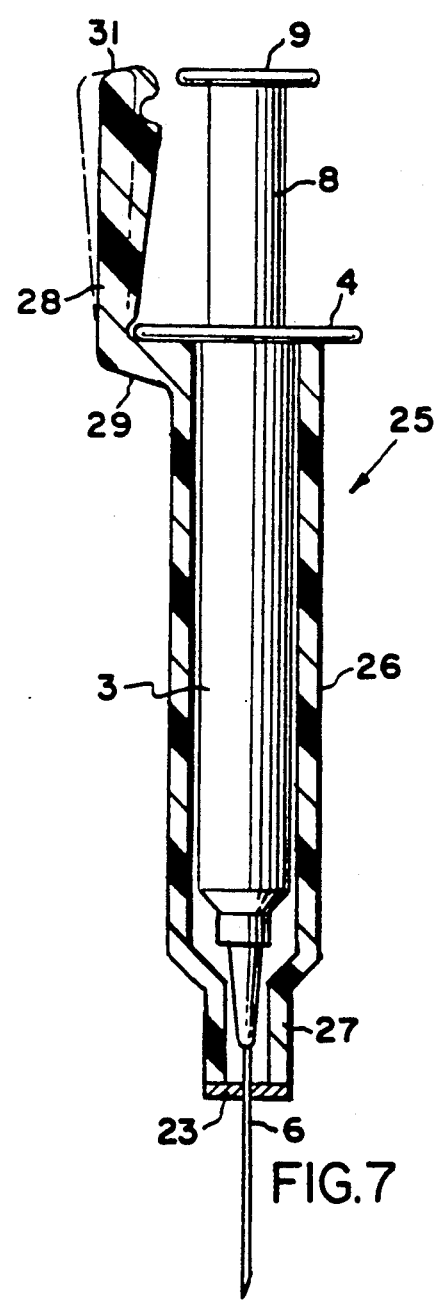
FIG. 7 is a vertical sectional view showing the apparatus of FIG. 5 in adjusted condition.

To extend the needle 6 from the safety position to the ready position, the extension 28 is manually deflected outwardly to the position shown in dotted lines in FIG. 7 so as to disengage the flange 4 from the groove 33. The barrel 3 then may be pushed downwardly through the body 12 to cause the needle 6 to pierce the membrane 23 and be extended from the body 12. The ability of the extension 28 to be deflected from its latching position to its unlatching position is enhanced by the groove 30.

Instead of deflecting the extension 28 from its latching position to its unlatching position, the barrel 3 may be rotated so as to disengage the flange 4 from the groove 33. Since there is no abutment at either end of the groove 33, the flange 4 may be rotated in either of two opposite directions to disengage it from the groove.

This disclosure is representative of presently preferred embodiments of the invention, but is intended to be illustrative rather than definitive thereof. The invention is defined in the claims.

I claim:

1. A hypodermic syringe comprising a tubular barrel having a fitting at one end thereof; a needle having a free end, said needle being secured at its other end to said fitting and extending in prolongation of said barrel; a piston slideably accommodated in said barrel for movement axially thereof; a tubular sheath member movably carried by said barrel and operable selectively to enclose and expose said one end of said needle, said sheath member comprising a hollow body member in one position of which said needle and at least a portion of said barrel are accommodated within said body member; and releasable latch means reacting between said body member and said sheath member for removably latching said body member in said one position, said latch means comprising a laterally extending flange on said body member, a single arcuate extension on said sheath member subtending an angle of not more than about 90°, and a groove in said extension for the removable accommodation of said flange.

2. The hypodermic syringe according to claim 1 wherein said barrel is rotatable relative to said extension between a first position in which said flange is accommodated in said groove and a second position in which said flange is removed from said groove.

3. The hypodermic syringe according to claim 2 wherein said flange is discontinuous circumferentially of said barrel member and said extension is correspondingly discontinuous.

4. The hypodermic syringe according to claim 3 wherein said flange has a peripheral length greater than that of said extension.

5. The hypodermic syringe according to claim 1 wherein said extension is deflectable to a position in which said flange is clear of said groove.

6. The hypodermic syringe of claim 1 wherein said sheath has a tip through which said distal end of said needle may pass, and a membrane sealing said tip, said distal end of said needle being capable of piercing said membrane.

7. A hypodermic syringe comprising a tubular barrel having at one end a needle extending in one direction longitudinally of said barrel and in prolongation thereof, said needle having a free distal end; a sheath having a tubular body of such length as to accommodate therein said needle in its entirety and at least a portion of said barrel, said portion of said barrel and said body being relatively rotatable; a single arcuate extension carried by said body and extending axially thereof in a direction opposite that in which said needle extends from said barrel; a laterally extending flange carried by said barrel at its opposite end, said extension having a circumferentially extending groove therein for the removable and slideable accommodation of said flange, said groove and said flange being of such relative circumferential lengths that said flange is movable in response to relative rotation of said barrel and said body between a first position in which said flange is accommodated in said groove thereby preventing relative axial movements of said barrel and said body and a second position in which said flange is clear of said groove thereby enabling relative axial movements of said barrel and said body a distance sufficient to extend said end of said needle beyond said sheath.

8. The hypodermic syringe according to claim 7 wherein said extension has a second annular slot axially spaced from the first mentioned groove for the accommodation of said flange when the latter is in said second position, thereby preventing relative axial movements of said barrel and said body.

9. The hypodermic syringe according to claim 8 wherein said groove has an abutment defining one end of said slot and against which said flange may seat to limit relative rotation in one direction of said barrel and said body.

10. They hypodermic syringe according to claim 8 wherein said extension is of such resilience as to be deflected to a position in which said flange is clear of said groove.

11. The hypodermic syringe according to claim 8 wherein said extension is resiliently biased in a direction toward said barrel.

12. The hypodermic syringe according to claim 11 wherein said extension is biased in a direction toward said body by a resilient hinge which couples said extension to said body.

13. The hypodermic syringe according to claim 8 wherein said groove is unobstructed at each of its ends.

14. The hypodermic syringe according to claim 7 wherein said sheath has a tip through which said distal end of said needle may pass, and a membrane sealing said tip, said distal end of said needle being capable of piercing said membrane.

15. A hypodermic syringe comprising a tubular barrel having at one end a needle extending in one direction longitudinally and in prolongation thereof, said needle terminating in a free distal end; a sheath having a tubular body of such length as to accommodate therein said needle in its entirety; an extension carried by said body and extending axially thereof in a direction opposite that in which said needle extends from said barrel; cooperable latch means carried by said barrel and said extension for releasably latching said barrel and said sheath in a safety position in which said distal end of said needle is wholly within the confines of said sheath; and resilient means coupling said extension to said sheath and enabling deflection of said extension in a direction to disengage said latch means and permit movement of said distal end of said needle out of said sheath.

16. The hypodermic syringe according to claim 15 wherein said latch means comprises a flange on said barrel and a groove in said extension, said flange being accommodated in said groove when said sheath is in said safety position.

17. The hypodermic syringe according to claim 15 wherein said resilient means comprises a hinge.

18. The hypodermic syringe according to claim 15 wherein said sheath has a tip through which said distal end of said needle may pass, and a membrane sealing said tip, said distal end of said needle being capable of piercing said membrane.

* * * * *